(12) United States Patent
Hamilton et al.

(10) Patent No.: US 10,953,188 B2
(45) Date of Patent: Mar. 23, 2021

(54) GAS THERAPY SYSTEM (71) Applicant: Fisher & Paykel Healthcare Limited, Auckland (NZ)

(72) Inventors: Mark Samuel Hamilton, Auckland (NZ); Jason Allan Klenner, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 1157 days.

(21) Appl. No.: 14/987,578

(22) Filed: Jan. 4, 2016

(65) Prior Publication Data
US 2016/0199605 A1 Jul. 14, 2016

Related U.S. Application Data (60) Provisional application No. 62/101,793, filed on Jan. 9, 2015.

(51) Int. Cl.
*A61M 16/00* (2006.01)
*A61M 16/16* (2006.01)
*A61M 16/10* (2006.01)

(52) U.S. Cl.
CPC ........ *A61M 16/16* (2013.01); *A61M 16/0069* (2014.02); *A61M 16/022* (2017.08); *A61M 16/109* (2014.02); *A61M 16/1095* (2014.02); *A61M 16/107* (2014.02); *A61M 16/1045* (2013.01); *A61M 2016/0021* (2013.01); *A61M 2016/0027* (2013.01); *A61M 2016/0039* (2013.01); *A61M 2205/42* (2013.01); *A61M 2205/505* (2013.01); *A61M 2205/8206* (2013.01); *A61M 2209/082* (2013.01); *A61M 2230/432* (2013.01)

(58) Field of Classification Search
CPC .. A61M 16/00; A61M 16/16; A61M 16/0003; A61M 16/0057; A61M 16/0063; A61M 16/0066; A61M 2209/082; A61M 2209/08; A62B 25/00; A62B 9/04; F16M 13/02; F16M 13/30; F24F 13/30; F24F 13/32
See application file for complete search history.

(56) References Cited

U.S. PATENT DOCUMENTS

| 4,460,143 A * | 7/1984 | Ohama | A61M 5/1417 215/399 |
| 6,065,649 A * | 5/2000 | Scoggins | A47K 5/1214 141/106 |
| 2006/0081242 A1* | 4/2006 | Han | A61M 16/16 128/200.24 |
| 2006/0144396 A1* | 7/2006 | DeVries | A61M 16/026 128/204.21 |

(Continued)

FOREIGN PATENT DOCUMENTS

WO WO-2009095611 A2 * 8/2009 ........... A61G 7/0503

*Primary Examiner* — Margaret M Luarca
(74) *Attorney, Agent, or Firm* — Knobbe Martens Olson and Bear, LLP (57) ABSTRACT

A flow generator for use in respiratory therapy can be constructed with a housing. A support fixation arrangement can be fixed to the housing. The support fixation arrangement can have a tab having an aperture that may be fitted over a hook extending from a support structure. The tab can be fixed to the housing such that it is manually liftable or pivotable about a plane.

18 Claims, 9 Drawing Sheets

(56) References Cited

U.S. PATENT DOCUMENTS

| | | | | |
|---|---|---|---|---|
| 2007/0045152 A1* | 3/2007 | Kwok | ............... | A61M 16/00 206/733 |
| 2008/0251081 A1* | 10/2008 | Claussen | ............ | A41D 13/1115 128/205.27 |
| 2009/0194101 A1* | 8/2009 | Kenyon | ............ | A61M 16/0057 128/201.22 |
| 2012/0152255 A1* | 6/2012 | Barlow | ............ | A61M 16/0066 128/205.25 |
| 2012/0167879 A1* | 7/2012 | Bowman | ........... | A61M 16/0066 128/201.22 |
| 2014/0137870 A1* | 5/2014 | Barlow | ............ | A61M 16/0057 128/205.25 |
| 2015/0023782 A1* | 1/2015 | Velzy | ................. | A61M 16/107 415/119 |
| 2015/0040908 A1* | 2/2015 | Goff | ................. | A61M 16/0057 128/205.24 |
| 2016/0184539 A1* | 6/2016 | Suzuki | ................ | F04D 29/664 128/205.25 |

* cited by examiner

GAS THERAPY SYSTEM

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Technical Field

The present disclosure generally relates to an apparatus for providing respiratory gas therapy.

Description of the Related Art

In patients suffering from obstructive sleep apnea (OSA), muscles that normally keep the upper airway open relax during slumber to the extent that the airway is constrained or completely closed off, a phenomenon often manifesting itself in instances of perceptible cessation of breathing or episodes of snoring. When this blockage of the airway occurs for a period of time, the patient's brain typically recognizes the threat of hypoxia and partially wakes the patient in order to open the airway so that normal breathing may resume. The patient may be unaware of these waking episodes or of associated blockages of the airway, which may occur as many as several hundred times per session of sleep. This partial awakening may significantly reduce the quality of the patient's sleep, over time potentially leading to a variety of symptoms, including excessive daytime sleepiness, chronic fatigue, elevated heart rate, elevated blood pressure, weight gain, headaches, irritability, depression and anxiety.

Obstructive sleep apnea is commonly treated with the application of positive airway pressure (PAP) therapy. PAP therapy involves delivering a flow of gas to a patient at a therapeutic pressure above atmospheric pressure that will reduce the frequency and/or duration of apneas, hypopneas, and/or flow limitations. The therapy is often implemented by using a positive airway pressure device to deliver a pressurized stream of air through a conduit to a patient through a patient interface or mask positioned on the face of the patient. A gases humidifier may be used to humidify gases being delivered to the patient.

SUMMARY

Flow generators, including but not limited to those used for PAP therapy, high flow therapy and ventilation therapy, are generally positioned close to a patient's bed or resting environment. A length of tubing generally extends from the flow generator to connect the flow generator to a patient interface worn by the patient. If, for example, the patient is supine and the flow generator is to the right or left of the patient (e.g. on a nightstand next to a bed), if the patient rolls or moves his head during slumber, forces may be exerted on the length of tubing, causing the tubing to move. If the length of tubing used is relatively short or if the tubing used is relatively stiff, the movement of the tubing can exert forces on the patient interface, potentially disrupting the sealing or fit of the patient interface on the patient's head. The patient must then re-adjust or reattach the patient interface to maintain the efficacy of the therapy, potentially causing stress to the patient and reducing the patient's compliance to a recommended therapy regime. Additionally, the movement of the tubing can exert forces on the flow generator, causing it to slide or fall, which can create unnecessary noise or damage the flow generator. Even if ample tubing is used together with the flow generator, in some cases the positioning of the flow generator on the left or right of the patient can cause the length of tubing to fall on the face or body of the patient during use, potentially causing discomfort. Relatively long lengths of tubing can have a relatively high flow resistance, which can promote the generation of excess noise, and long lengths of tubing may be more likely to become tangled in use. Additionally, long lengths of tubing may be more likely to exert force on the patient interface or flow generator due to their weight, particularly if there is an unsupported length of tubing between, for example, the patient interface and the nightstand. Solutions for the above difficulties are sought.

Thus, in accordance with certain features, aspects and advantages of at least one of the embodiments disclosed herein, a respiratory therapy apparatus is disclosed. The respiratory therapy apparatus comprises a breathing assistance component, a housing adapted to house the breathing assistance component, and a support fixation arrangement adapted to attach the respiratory therapy apparatus to a support.

In some embodiments, the breathing assistance component comprises one or more of a blower unit, a gases humidifier, a sensor, a conduit, a filter, a fluid reservoir, and a connector.

In some embodiments, at least a portion of the support fixation arrangement is fixed to or integrally formed with the housing.

In some embodiments, the respiratory therapy apparatus comprises a lid to close an opening of the housing providing access to the breathing assistance component, and the support fixation arrangement is fixed to or integrally formed with the lid.

In some embodiments, the housing further comprises a gases outlet, and the lid is located at a first end of the respiratory therapy apparatus and the gases outlet is located at a second end of the respiratory therapy apparatus opposite the first end.

In some embodiments, the housing further comprises a gases outlet, and the support fixation arrangement is adapted to be attached to a support such that when attached the gases outlet is oriented vertically downwards.

In some embodiments, the housing further comprises a gases outlet, and the support fixation arrangement is located at a first end of the respiratory therapy apparatus and the gases outlet is located at a second end of the respiratory therapy apparatus opposite the first end.

In some embodiments, the apparatus further comprises a gases inlet, wherein the gases inlet is oriented substantially perpendicularly to the gases outlet or to the support fixation arrangement when in a fixation position to attach the respiratory therapy apparatus to a support.

In some embodiments, the gases inlet comprises a plurality of gases inlets distributed about a perimeter of the housing.

In some embodiments, the plurality of gases inlets is substantially evenly distributed about the perimeter.

In some embodiments, the support fixation arrangement is configured to allow the respiratory therapy apparatus to hang from the support, for example from a hook structure extending from the support.

In some embodiments, the support fixation arrangement comprises a movable tab secured at a first end of the tab to the housing, or wherein the respiratory therapy apparatus comprises lid to close an opening of the housing and the support fixation arrangement comprises a movable tab secured at a first end of the tab to the lid, the movable tab movable between a non-fixation position and a fixation position to attach the respiratory therapy apparatus to a support.

In some embodiments, the tab is liftable or pivotable or bends from the non-fixation position to the fixation position to attach the respiratory therapy apparatus to a support.

In some embodiments, the tab rests in a recess present on the housing or the lid when in the non-fixation position.

In some embodiments, the tab is removably attached to the housing or lid, or alternatively is permanently attached to the housing or lid, for example integrally formed with the housing or lid.

In some embodiments, the tab comprises a first retention element that interfaces with a second retention element on the housing or the lid to secure the tab to the housing or the lid.

In some embodiments, the first retention element comprises a ribbed structure and the second retention element comprises an aperture, the ribbed structure contracting and expanding when forced through the aperture to secure the tab to the housing or the lid.

In some embodiments, the tab comprises an aperture adapted to accept a portion of the support.

In some embodiments, the housing or lid comprises a recessed portion below the aperture when the tab is in the non-fixation position so that the tab is manipulatable through the aperture to move the tab from the non-fixation position to the fixation position.

In some embodiments, the tab is formed from a resilient material.

In some embodiments, the housing is substantially cylindrical or elliptically cylindrical.

BRIEF DESCRIPTION OF THE DRAWINGS

Specific embodiments and modifications thereof will become apparent to those skilled in the art from the detailed description herein having reference to the figures that follow, of which.

DETAILED DESCRIPTION

Figure 1:
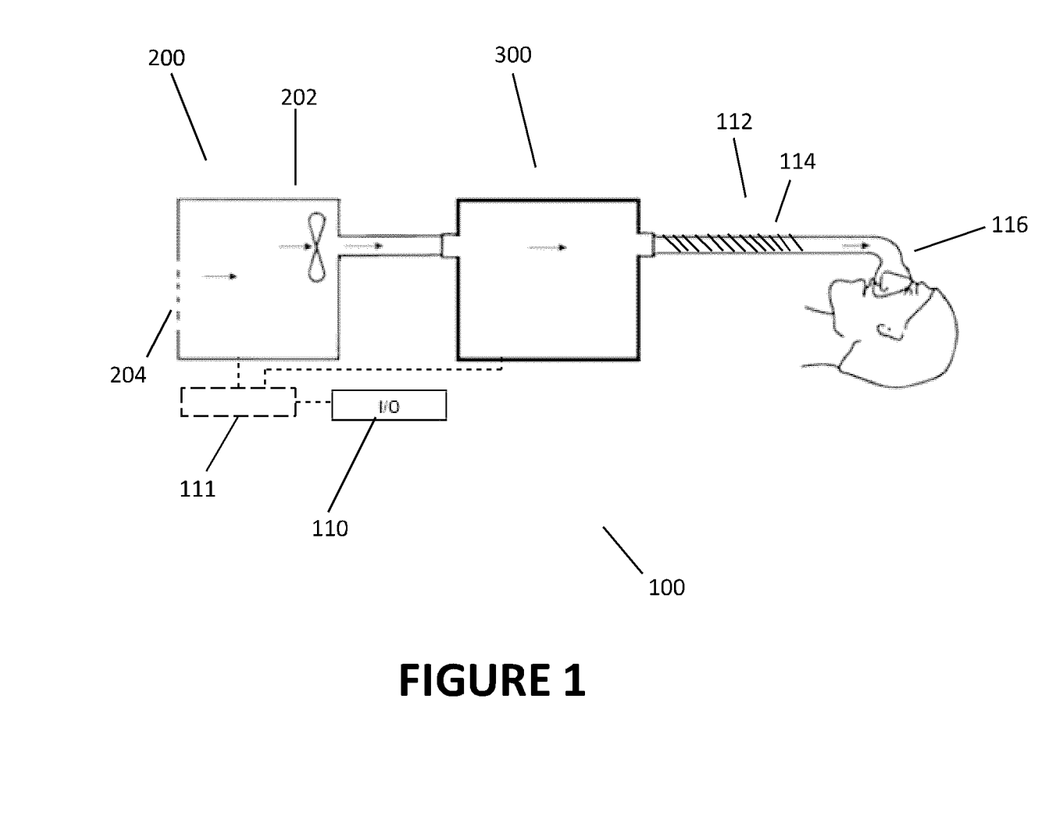
FIG. 1 shows a schematic diagram of a respiratory therapy system.

With reference to the non-limiting exemplary embodiment illustrated in FIG. 1, a respiratory therapy system 100 is shown. The respiratory therapy system 100 comprises a flow generator 200. The flow generator 200 comprises a PAP device. The flow generator 200 comprises a housing 202. The flow generator 200 receives gases from a gases inlet 204. Gases received by the flow generator 200 are propelled towards a user. In the illustrated configuration, the flow generator 200 transfers the received gases to a gases humidifier 300. The gases humidifier 300 humidifies the gases. The gases humidifier 300 may also heat the gases. Humidified gases are passed from a humidifier outlet to a gases conduit 112. The gases conduit 112 comprises a heater 114. The heater 114 reduces or prevents the condensation of moisture along the walls of the gases conduit 112. Gases are passed from the gases conduit 112 to a patient interface 116 through which they are delivered to a user. The respiratory therapy system 100 comprises a controller 111 that controls the operation of the flow generator 200. The controller 111 also controls the operation of the gases humidifier 300. The respiratory therapy system 100 comprises an input/output (I/O) module 110. The I/O module 110 comprises a way for a user to interact with and set parameters for the flow generator 200 and/or gases humidifier 300 (e.g. through the controller 111) as well as receive information regarding the operation of the respiratory therapy system 100 and/or its components. The I/O module 110 may comprise, for example, buttons, knobs, dials, switches, levers, touch screens, speakers, displays and/or other input or output elements. In some configurations, the I/O module 110 may be adapted to communicate with the controller 111 via a physical data connection (e.g. via a wire, etc). In other configurations, the I/O module 110 may be adapted to communicate with the controller 111 via a wireless data connection (e.g. via Bluetooth, WiFi, etc). In other configurations, the gas conduit 112 may not have a heater 114. In other configurations, the gases humidifier 300 may not be present, and the flow generator 200 may interface with the patient interface 116 (e.g. either directly or via the gases conduit 112). In other configurations, the I/O module 110 may not be present. In some such configurations, the flow generator 200 may be controlled dependent on the determination of a patient usage signal (e.g. via sensing of respiratory activity through the use of a flow or pressure sensor, sensing of exhaled carbon dioxide using a CO2 sensor, etc). In other such configurations, the flow generator 200 may only have one therapy setting that is automatically utilized when the flow generator 200 receives energy from a power source. In some configurations the flow generator 200 comprises a motorized blower or compressor.

The flow generator 200 and gases humidifier 300 may be part of an integrated flow delivery system or may share a housing. In other configurations, the flow generator 200 may comprise components other than PAP devices, including but not limited to high flow therapy devices or ventilation devices. If a PAP device is utilized, the PAP device may comprise a number of PAP device variants, including but not limited to continuous positive airway pressure (CPAP) devices, automatically adjusting positive airway pressure (APAP or AutoPAP) devices or bi-level positive airway pressure (BiPAP or bi-level PAP) devices. The patient interface 116 comprises a mask adapted to seal about and channel gases to the nose and/or mouth of the user. In other configurations, the patient interface 116 may comprise a semi-sealing or non-sealing interface. In other configurations the patient interface 116 may comprise an oral mask, an oronasal mask, a full face mask, a nasal pillows mask, a nasal cannula, an endotracheal mask or tube, combinations of the above, or other gas conveying elements, apparatus or systems.

Further attention is given to the flow generator 200. As shown in the non-limiting exemplary embodiment illustrated in FIGS. 2A-2F, the flow generator 200 comprises a housing or shell 202. In some embodiments the housing is rigid. The housing 202 houses a blower unit 210 (shown schematically in FIG. 2D). The blower unit 210 comprises a motorized blower. The motorized blower can have a number of different configurations, including but not limited to the blower configurations disclosed in commonly-owned WO2013/009193, which is hereby incorporated by reference in its entirety. In other configurations, the blower unit 210 can comprise bellows arrangements or a pressurized gas container fitted with a valve adapted to provide for the output of controlled flows of gases. In other configurations, the housing 202 may not be rigid. For example, in some configurations the housing 202 may be at least partially soft, flexible or resilient.

Figure 2A:
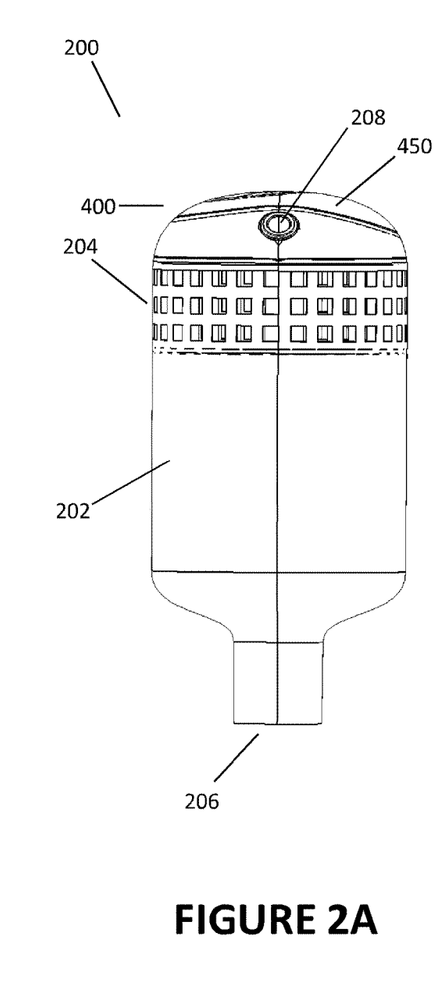
FIG. 2A shows a front view of a flow generator.
Figure 2B:
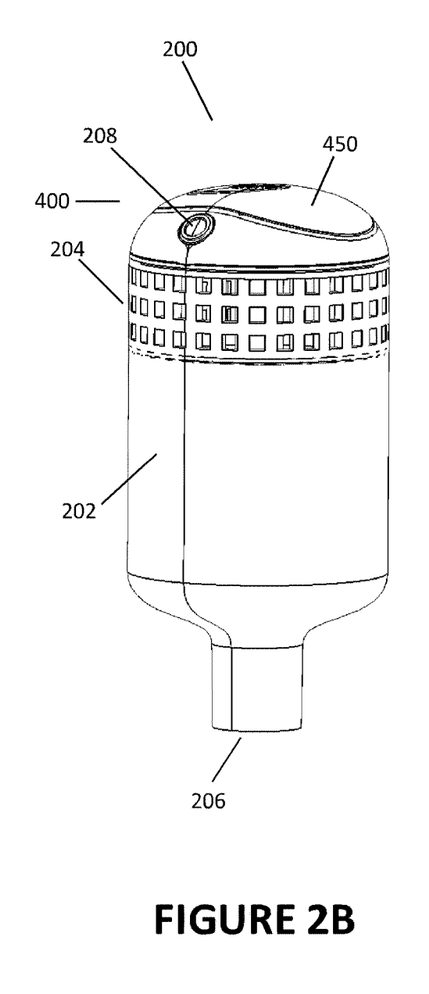
FIG. 2B shows a front-side view of the flow generator of FIG. 2A.
Figure 2C:
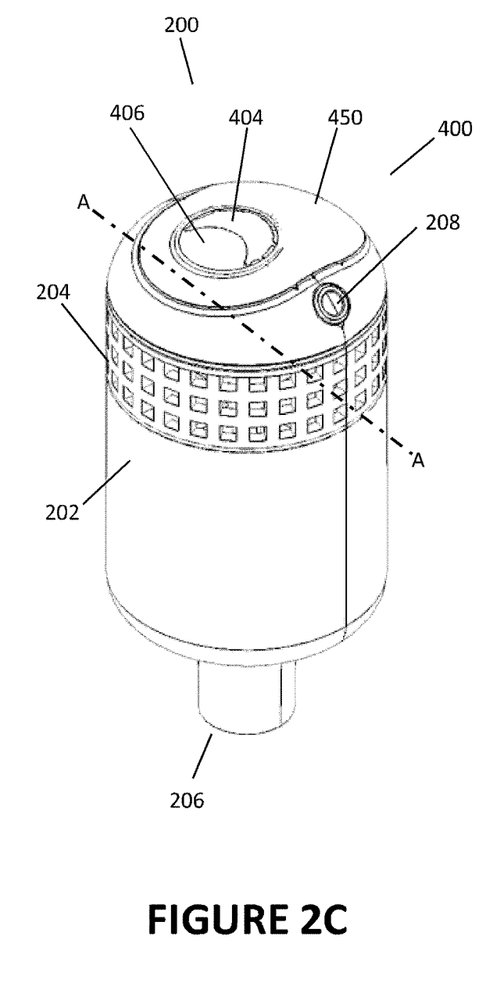
FIG. 2C shows a perspective view of the flow generator of FIG. 2A.
Figures 2D, 2E, 2F:
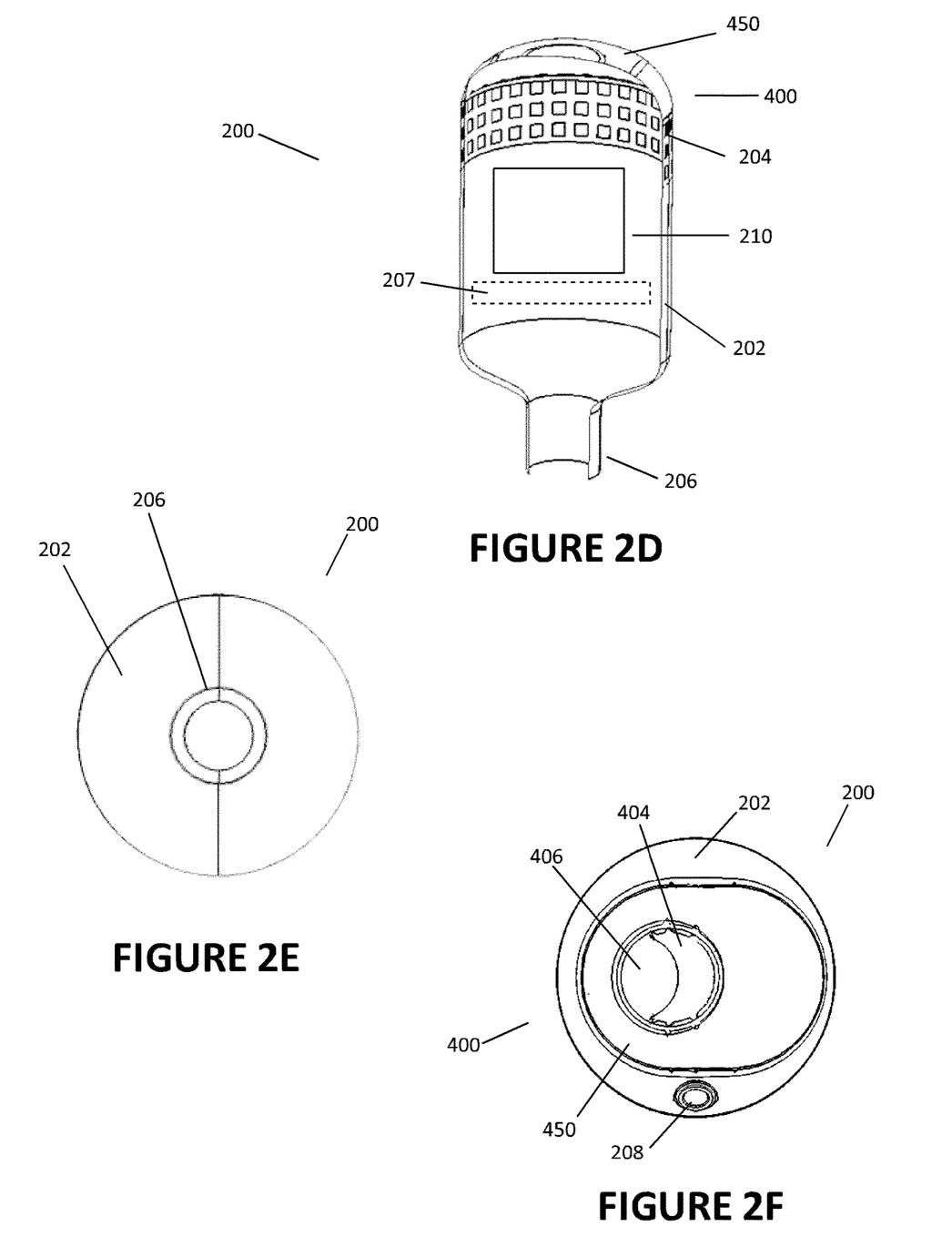
FIG. 2D shows a cross-sectional view of the flow generator of FIG. 2A along line A-A as viewed in FIG. 2C.
FIG. 2E shows a bottom view of the flow generator of FIG. 2A.
FIG. 2F shows a top view of the flow generator of FIG. 2A.

In some configurations, and as shown schematically in FIG. 2D, the housing 202 also houses a gas conditioning element 207. The gas conditioning element 207 is positioned downstream of the blower unit 210 and is configured to treat flows propelled by the blower unit 210. The gas conditioning element 207 may, for example, heat, humidify, filter, muffle and/or otherwise treat flows propelled by the blower unit 210. The gas conditioning element 207 may comprise a pass-over type humidifier (e.g. the gases humidifier 300 described elsewhere in this disclosure with reference to FIG. 1), a sorbent medium that may be moistened before use of the flow generator 200 (for example, a sponge or other porous sorbent medium), a heat-and-moisture exchange (HME) apparatus or medium, a heat exchange medium, a filter, a muffler, and/or another apparatus, system or material configurable to treat gases exiting the blower unit 210. In other configurations, the gas conditioning element 207 could be positioned upstream of the blower unit 210. In still other configurations, the gas conditioning element 207 may be omitted.

The housing 202 comprises a gases inlet portion. The gases inlet portion of the housing 202 comprises a gases inlet. In some embodiments the gases inlet comprises a plurality of gases inlets 204. The gases inlets are distributed about a perimeter of the housing 202. In the illustrated configuration, the housing 202 comprises three rows of gases inlets substantially evenly distributed about the perimeter of the housing 202. In other words, each gases inlet in a row is substantially equidistant from adjacent gases inlets in the same row. In some configurations, each gases inlet is also substantially equidistant from adjacent gases inlets in adjacent rows. In other configurations, other numbers of rows, including but not limited to two rows or a single row of gases inlets, may be used. Arranging the gases inlets about the perimeter of the housing 202 can have a number of advantages. Arranging the gases inlets about the perimeter can help to ensure that at least some of the gases inlets 204 are not obstructed by adjacent walls or support surfaces. Even if the support fixation arrangement 400 (described elsewhere in this disclosure with reference to the accompanying figures) is not employed, the distribution of the gases inlets may allow the flow generator 200 to be used when lying on its side on any available surface. In some cases, the illustrated gases inlet arrangement can reduce the perceived noise of the flow generator 200. Additionally, the aesthetic appeal of the flow generator 200 may be improved, which may in turn improve the therapy regime compliance of a user using the flow generator 200.

In some configurations, the gases inlets may be covered or insulated with noise attenuating structure or elements (including but not limited to open cell foams or 'honeycomb' structures) to reduce noise generated by flow passing through the gases inlet or inlets 204. In some configurations, one or more gas filters may be positioned at or near the gases inlet or inlets 204. The gas filters may remove contaminants or pollutants from the incoming gas stream. The gas filters may be anti-pathogenic (e.g. anti-bacterial, anti-viral, anti-fungal, etc).

In other configurations, the gases inlet 204 may comprise a single gases inlet. The single gases inlet may be positioned on a single side of the housing 202, or may extend at least partway around the perimeter of the housing 202, or may extend around the full perimeter of the housing.

The housing 202 comprises a gases outlet 206. The gases outlet 206 is adapted to interface with a tube or gases conduit (for example, the gases conduit 112 described elsewhere in this disclosure with reference to FIG. 1). The gases outlet 206 is oriented substantially perpendicularly relative to the gases inlet or inlets 204 of the housing. In other words, gases entering the flow generator 200 in a first direction through the gases inlet 204 generally leave the flow generator 200 through the gases outlet 206 in a second direction substantially perpendicular to the first direction. In use, the illustrated gases outlet 206 is configured to face vertically downwards (described in further detail elsewhere in this disclosure with reference to the accompanying figures). In other configurations the gases outlet 206 may be positioned elsewhere on the housing 202.

The flow generator 200 comprises an electrical connector 208. The electrical connector 208 is adapted to allow components of the flow generator 200 on or within the housing 202 (including but not limited to the blower unit 210 and/or the gas conditioning element 207) to receive electrical energy from a mains power supply. In other configurations, the flow generator 200 may instead receive power from a battery. The battery may be stored within the housing or may be joined to the housing. In such configurations the electrical connector 208 may not be present.

The flow generator 200 comprises a support fixation arrangement 400. The support fixation arrangement 400 is configured to allow the flow generator 200 to be joined to a support structure. In the illustrated configuration, the support fixation arrangement 400 is configured to allow the flow generator 200 to hang from a support structure (e.g. from a hook structure extending from the support structure). Further details regarding the support fixation arrangement 400 are described elsewhere in this disclosure with reference to the accompanying figures.

Figure 3A:
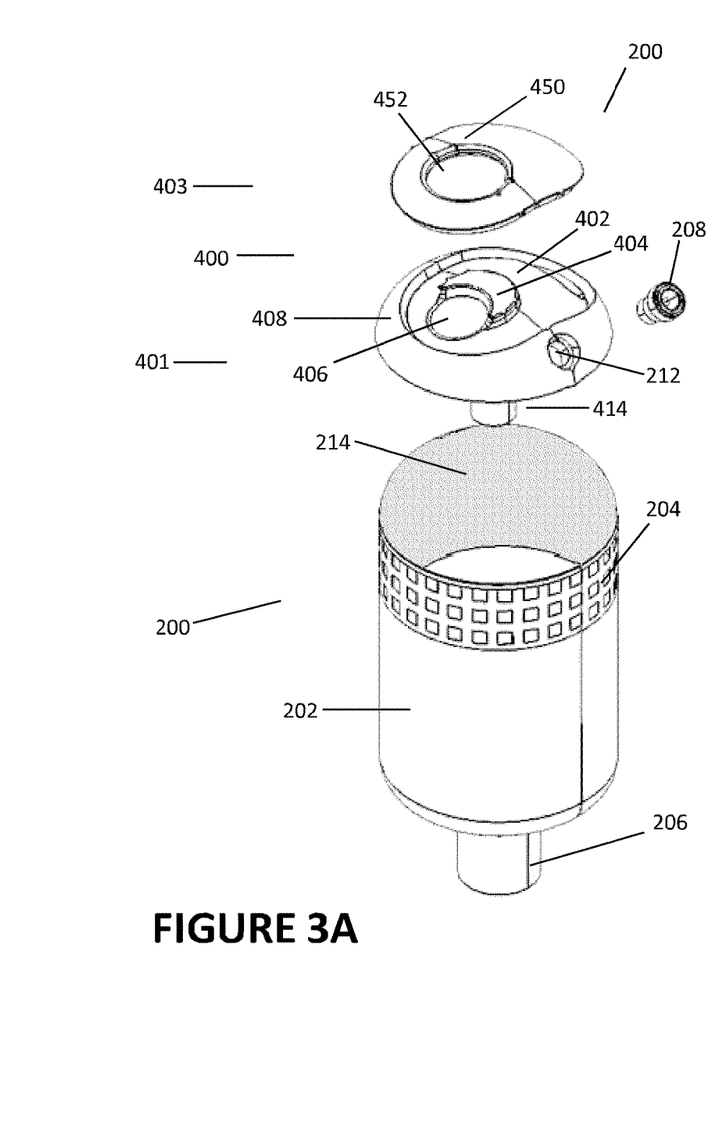
FIG. 3A shows an exploded perspective view of a flow generator.
Figure 3B:
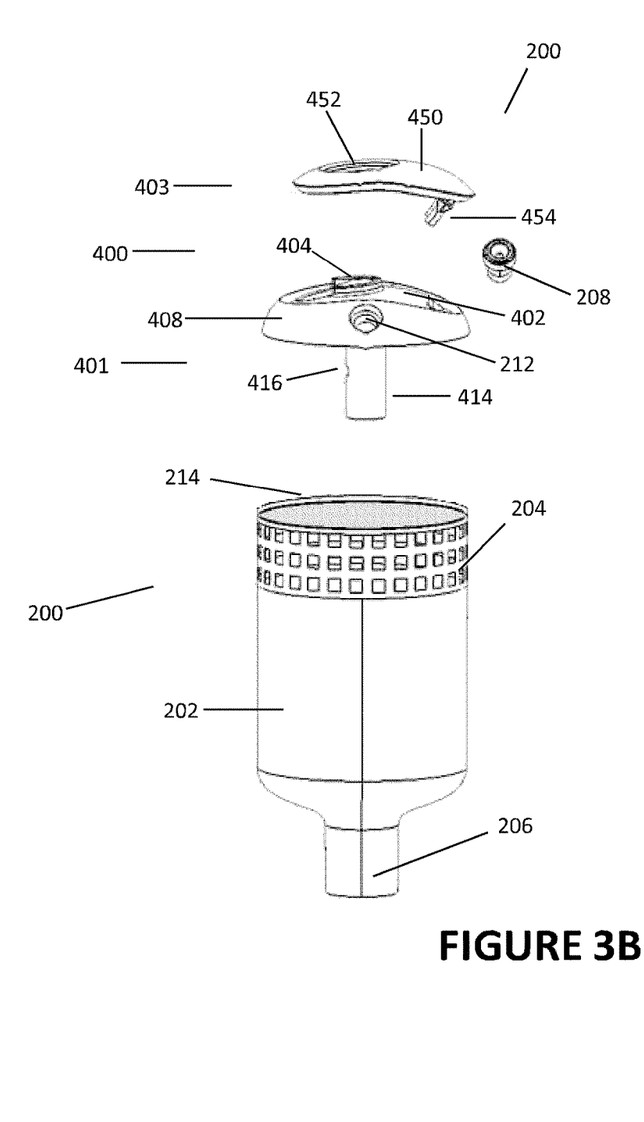
FIG. 3B shows an exploded side view of the flow generator of FIG. 3A.
Figure 4A:
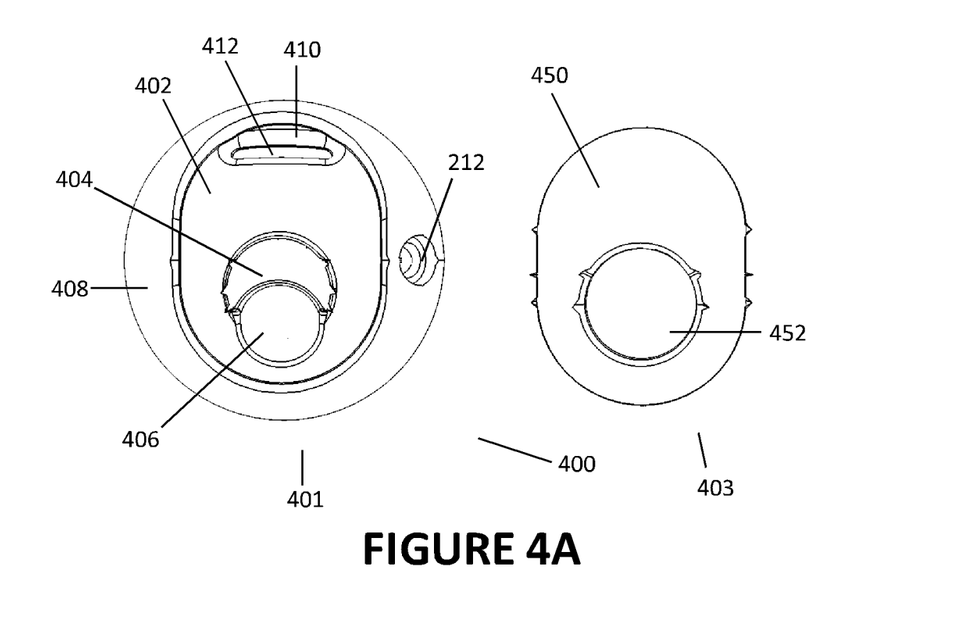
FIG. 4A shows an exploded top view of a support fixation arrangement.
Figure 4B:
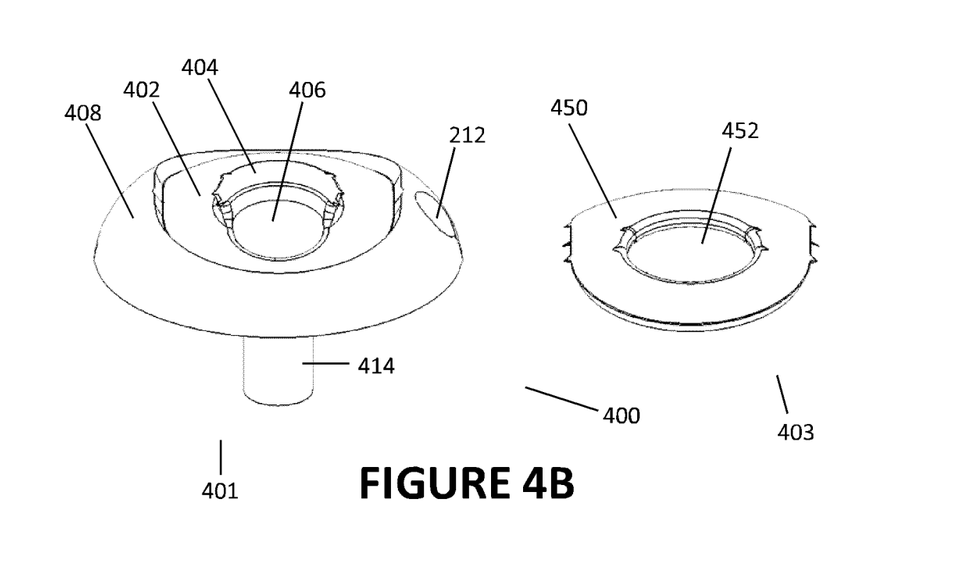
FIG. 4B shows an exploded elevated front view of the support fixation arrangement of FIG. 4A.

With reference to FIG. 3A, an exploded view of the flow generator 200 is shown. The flow generator 200 further comprises a lid 408. The lid is provided to close an opening of the housing. The opening provides access to the blower unit inside the housing. As illustrated in FIGS. 3A and 3B, in some embodiments the lid is located at a first end of the housing and the outlet is located at a second end of the housing that is opposite the first end. In some embodiments the lid 408 comprises a stem 414 that fits in a corresponding aperture 214 present in the housing 202 to secure the lid 408 to the housing 202 (for example, via a snap fit connection realized through the use of a notch 416 present on the stem 414 and a corresponding protrusion on an interior surface of the housing 202). Other ways of securing the lid 408 to the housing 202, including but not limited to bayonet-type connections, alternative snap fit connections, screw threads or hinging connections, may be used. The lid 408 is configured to seal a gases flow passageway within the housing 202 when secured to the housing 202 (e.g. through the use of various structures including but not limited to sealing membranes, collars, or O-rings). The lid 408 additionally comprises a hole 212 in which the electrical connector 208 may be located to allow for power to be supplied to the flow generator 200 or components of the flow generator 200. In some embodiments the lid 408 is removably attachable to the housing 202. Opening the lid 408 may allow access to components of the flow generator 200, including but not limited to the blower unit 210 and the gas conditioning element 207, if present. In some embodiments the lid 408 comprises the support fixation arrangement 400. In other configurations, the lid 408 is permanently attached to the housing 202. In still other configurations, there is no lid 408 and the housing 202 is substantially closed over the portion of the flow generator 200 that would have been covered by the lid 408. The housing 202 may then comprise the support fixation arrangement 400.

The support fixation arrangement 400 comprises a stationary component 401 and a movable component 403. In some embodiments, the stationary component 401 is fixed to or integrally formed with the lid 408. In other words, in some embodiments the lid is the stationary component of the fixation arrangement 400. In other configurations, the stationary component 401 can be fixed to or integrally formed with the housing 202, or in other words the housing is the stationary component of the fixation arrangement. The stationary component 401 acts as a base or support for the movable component 403 of the fixation arrangement. In some embodiments, the movable component 403 is detachably connected to the stationary component 401. The movable component 403 is adapted to move (e.g. rotate, cantilever, pivot, bend (for example elastically bend), move laterally, move axially or move transversely relative to the housing 202 and/or lid 408) such that it can interface or join (attach) with a support structure. The movable component 403 of the support fixation arrangement 400 is configured such that when the movable component 403 interfaces or joins with or attaches to the support structure, the flow generator 200 hangs from at least a part of the support structure. In the exemplary non-limiting illustrated configurations, the movable component 403 is a liftable tab. The tab 403 is constructed from silicone or other resilient material that allows the tab to elastically flex between a fixation configuration and a non-fixation configuration. In some configurations, the liftable tab may be constructed from materials, including but not limited to, flexible or rigid plastics, metals, fabrics, or foams. The movable component 403 comprises an aperture 452 adapted to receive at least a part of the support structure. The function of the aperture 452 is further described elsewhere in this disclosure with reference to the accompanying figures.

With reference to FIGS. 3A-4B, the stationary component 401 comprises a recessed region 402 in which a body 450 of the moving component 403 lies. In some embodiments, the moveable component comprises a first retention element and the stationary component 401 comprises a second retention element. The first and second retention elements are adapted to interface together to connect the moveable component 403 to the stationary component 401. In the illustrated configuration, the second retention element comprises an aperture 412 that extends through the recessed region 402 present on the stationary component, and the first retention element comprises a projection 454 that extends from the body 450 of the moving component 403.

Figure 5A:
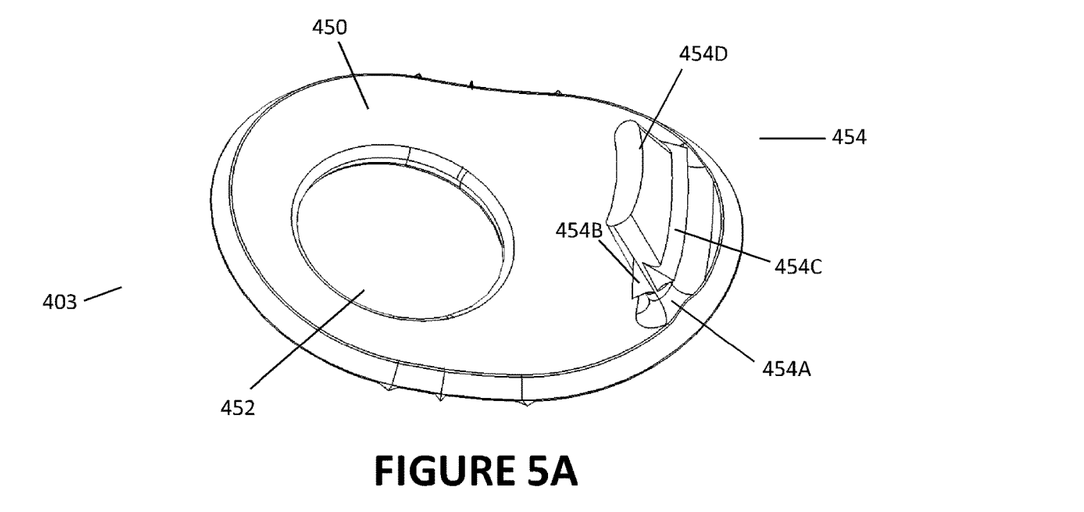
FIG. 5A shows an elevated front view of a portion of a support fixation arrangement.
Figure 5B:
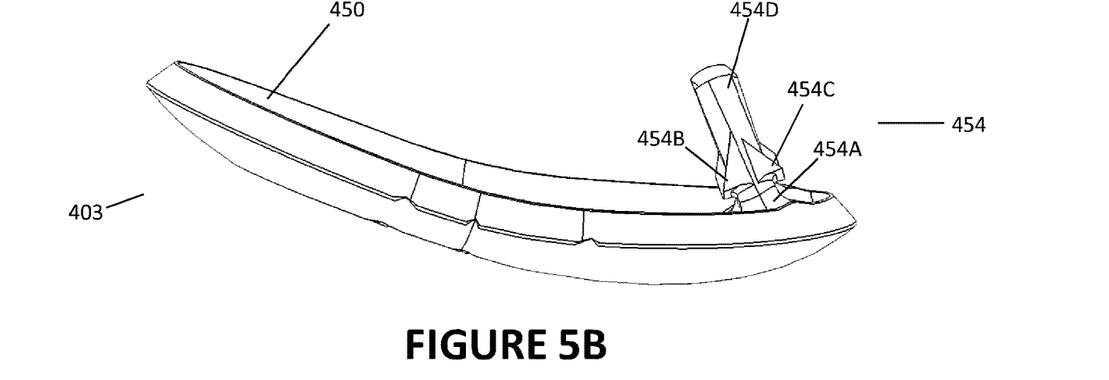
FIG. 5B shows a side view of the portion of the support fixation arrangement of FIG. 5A.
Figure 6:
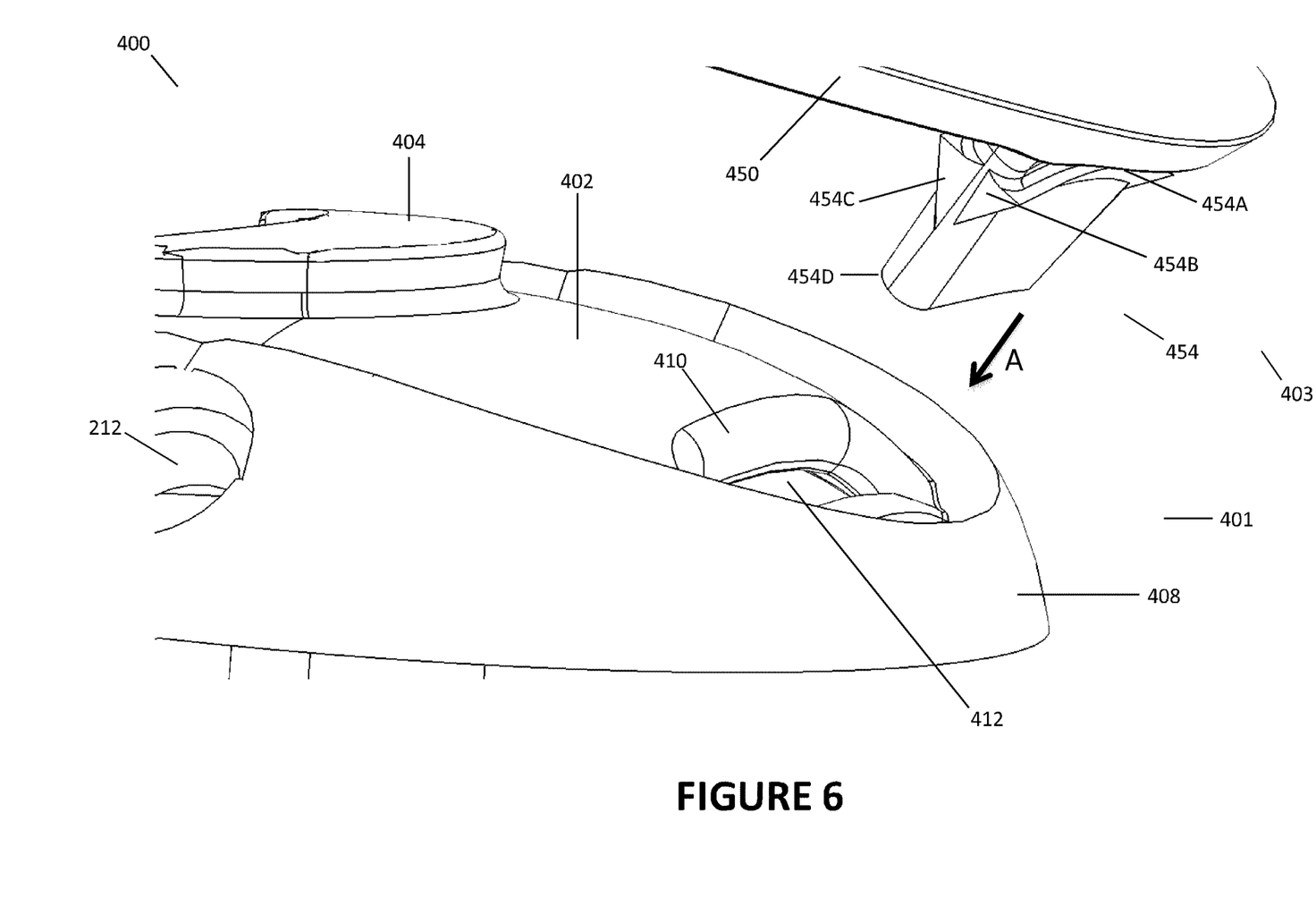
FIG. 6 shows an exploded elevated side view of a support fixation arrangement.

Another view of the retention elements is shown in FIGS. 5A-6. As shown, the projection 454 of the movable component 403 comprises a base 454A, a projecting end 454D axially distal from the base 454A, and a pair of ribs 454B, 454C located between the base 454A and the projecting end 454D. The ribs 454B, 454C are positioned substantially co-laterally along the axial length of the projection 454. Additionally, the ribs 454B, 454C are beveled such that they narrow in width as they extend along the axial length of the projection 454 towards the projecting end 454D (e.g. in a 'wedge' shape). The aperture 412 of the stationary component 401 is defined by a beveled or curved wall 410 that is angled or oriented towards an inside portion of the stationary component 401.

As the projection 454 is urged towards the aperture 412 (e.g. along arrow A shown in FIG. 6), the ribs 454B, 454C compress as they pass along the wall 410 defining the aperture 412 (the beveled or curved shape of the wall 410 encouraging the movement of the ribs 454B, 454C into the aperture 412). The ribs 454B, 454C then expand back into a neutral state when they clear the aperture 412, attaching the movable component 403 to the stationary component 401. Flat portions of the ribs 454B, 454C (shown in FIG. 6 at ends of the ribs 454B, 454C proximal to the base 454A) serve to resist detachment of the movable component 403 from the stationary component 401 when the components 403, 401 are joined. However, upon the exertion of sufficient force the flat portions of the ribs 454B, 454C may be deformed such that the movable component 403 may be detached from the stationary component 401. Removal of the movable component 403 from the stationary component 401 may be useful for replacement of the movable component 403 (for example, due to contamination or wear-and-tear of the movable component 403).

In other configurations, the projection 454 may comprise more than two ribs. In other configurations, the projection 454 may comprise a single rib. The single rib may be located on a side of the projection 454 or may be extend along part or all of a perimeter of the ribbed projection 454. Although the beveled or curved shape of the wall 410 defining the aperture 412 is useful for controlling the force necessary to attach the movable component 403 and the stationary component 401, in other configurations the wall 410 may comprise straight edges. It should be understood that other systems, arrangements, structures or elements may be used to join the movable component 403 and the stationary component 401, including but not limited to latches, catches, hinging structures, adhesives (e.g. resealable adhesives) or hook-and-loop patches. In still other configurations, the movable component 403 may be permanently attached to the stationary component 401. The movable component 403 may only be attached to the stationary component 401 at a portion of the movable component 403 (e.g at one end of the body 450 of the movable component 403) to allow for relative motion between the movable component 403 and the stationary component 401. For example the movable tab is secured at a first end of the tab to the stationary component.

Further referring to FIGS. 3A-4B, the stationary component 401 further comprises a raised portion 404 within the recessed region 402 of the stationary component 401. The raised portion 404 is elevated above a bottom of the recessed region 402 such that it is substantially flush with or above an upper surface of the stationary component around the recessed region 402. The raised portion 404 helps to maintain the orientation of the movable component 403 with respect to the stationary component 401 when the movable component 403 is in a non-fixation position on the stationary component 401. The stationary component 401 additionally comprises a recessed portion 406 within the recessed region 402. The recessed portion 406 is recessed relative to the recessed region 402 of the stationary component. The recessed portion 406 provides a space for a user to manipulate the movable component 403 so as to move the movable component 403 with respect to the stationary component 401. For example, a user may insert a finger through the aperture 452 of the movable component into the recessed portion 406 within the recessed region 402 and use the finger to lift a portion of the movable component 403 spaced from the first retention element of the movable component 403 relative to the stationary component. The raised portion 404 and recessed portion 406 improve the usability and convenience of the support fixation arrangement 400. However, in other configurations the raised portion 404 and recessed portion 406 may be omitted.

Figures 7A, 7B:
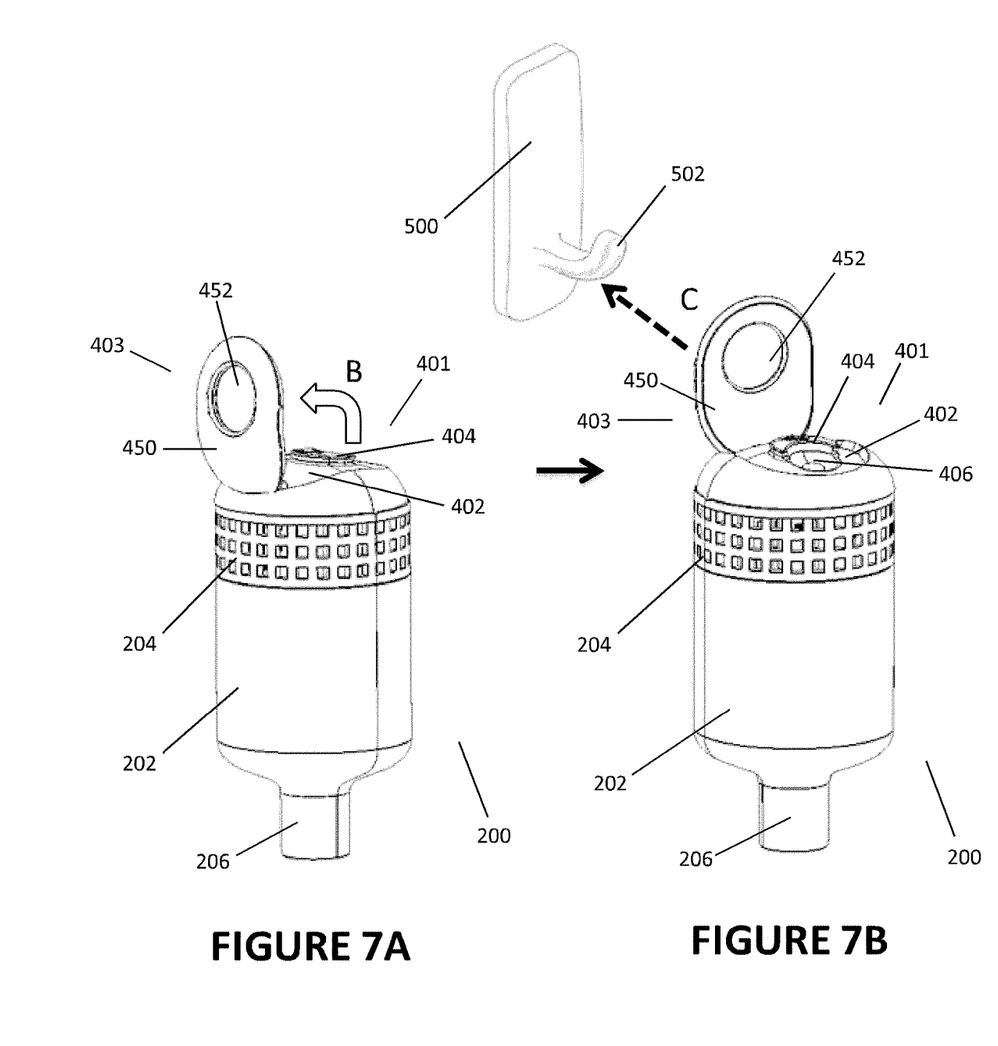
FIGS. 7A-7C show a possible usage of an exemplary support fixation arrangement secured to a flow generator.
Figure 7C:
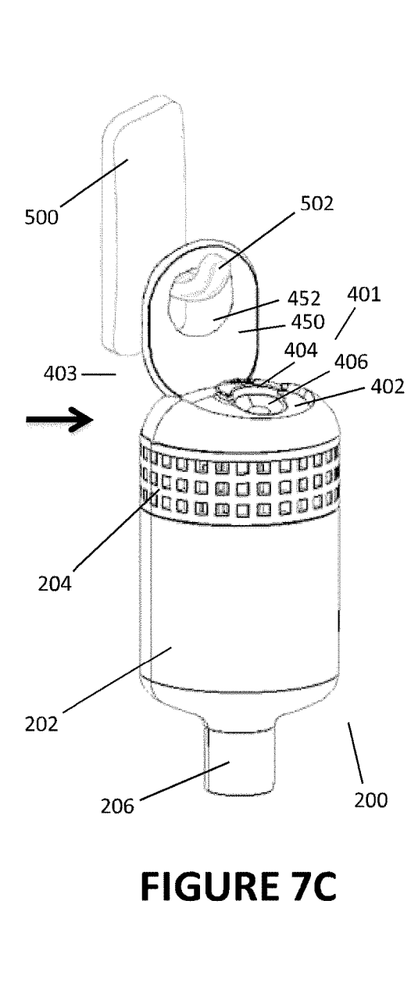

FIGS. 7A-7C show usage of a flow generator 200 according to an embodiment of the disclosure. In some embodiments, the support fixation arrangement 400 is located at a first end of the apparatus and the gases outlet is arranged at a second end of the apparatus opposite the first end. To use the support fixation arrangement 400, the body 450 of the movable component 403 can be moved (for example, by positioning a finger in the recessed portion 406 through the aperture 452 of the moveable component and lifting the body 450 to cause the body 450 to pivot or bend about the first retention element as shown using curved arrow B) from a neutral, resting position or non-fixation position to a fixation position. In the exemplary configuration, the body 450 is in a fixation position when the body 450 is oriented such that it extends outwardly from the stationary component 401 in a direction substantially parallel to or aligned with the gases outlet 206. In some embodiments, the body 450 is in a fixation position when the body 450 is oriented such that it extends outwardly from the stationary component 401 in a direction substantially perpendicular or at an angle to the gases inlet 204. When the body 450 is in the fixation position, the support fixation arrangement 400 can be attached to a support. In the exemplary non-limiting configuration, a support 500 having a hook or extension 502 is contemplated. The support 500 may, for example, be fixed to a wall, a bed frame, a bed post, a window, or another structure near a patient's resting or sleeping environment (e.g. integrally formed with the structure or fixed to the structure using, for example, adhesives). The aperture 452 present on the body 450 is moved towards the extension 502 (e.g. along arrow C shown in FIG. 7B) until the extension 502 is received within the aperture 452 (e.g. as illustrated in FIG. 7C). Once in place, the flow generator 200 hangs from the support 500 such that the gases outlet 206 is oriented vertically downwards (e.g. towards a sleeping or resting patient).

The exemplary non-limiting support fixation arrangement 400 allows the flow generator 200 to be conveniently located above a patient receiving therapy instead of on the left or right of the patient. Locating the flow generator 200 above the patient can reduce the tendency for tubing to rest on the patient's face, neck, chest or other parts of the body when the patient moves. Additionally, in the illustrated configuration the effects of the transfer of drag forces exerted on tubing extending from the gases outlet 206 to the flow generator 200 and/or patient interface 116 (see FIG. 1) may be mitigated. In some cases, a shorter length of tubing can be used, which can reduce flow resistance (which in turn can reduce perceptible noise), reduce forces exerted on the patient interface 116 (due to, for example, the weight of the tubing) and/or reduce the potential for tube tangling. The patient may move while resting or sleeping without needing to readjust the position of the patient interface 116 or the position of the tubing.

In some configurations, tubing that would be connected to the gases outlet 206 of the flow generator 200 may be integrally formed or in the form of a single continuous part together with the gases outlet 206. In some configurations, tubing used with the gases outlet 206 may be adapted to be extendible or collapsible to allow for management of the length of tubing used. For example, the tubing used could have a corrugated accordion-like configuration, or the tubing used could be present on a spool adapted to release lengths of tubing commensurate with the level of force applied to the tubing on the spool.

Other systems, arrangements, structures or elements adapted to allow the flow generator 200 to hang off or be suspended from a support 500 are contemplated. For example, in some configurations, the support fixation arrangement 400 may comprise an adhesive patch affixed to a side of the housing 202 that may be adhered to a support. In some configurations, the support fixation arrangement 400 may comprise a hook patch secured to a side of the housing 202 that can be fixed to a loop path secured to a support (e.g. in a hook-and-loop style connection system). In some configurations, the support fixation arrangement 400 may comprise suction cups secured to a side of the housing 202 that may be used to removably secure the housing 202 to a support. In some configurations, the support fixation arrangement 400 may comprise a magnet or magnetic surface that may be magnetically secured to a complementary magnet or magnetic surface located on a support. In some configurations, the movable component 403 of the support fixation arrangement 400 may comprise a karabiner-like structure that may be secured to an aperture located on a support.

Figure 8A:
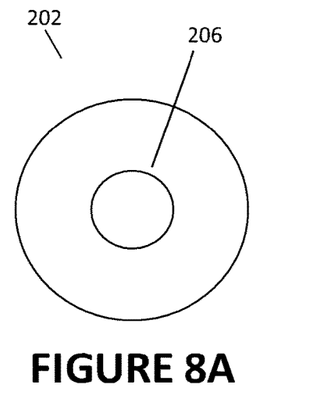
FIGS. 8A-8D show bottom views of exemplary flow generators.
Figure 8B:
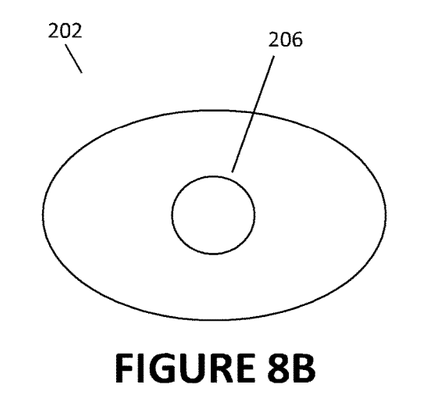
Figure 8C:
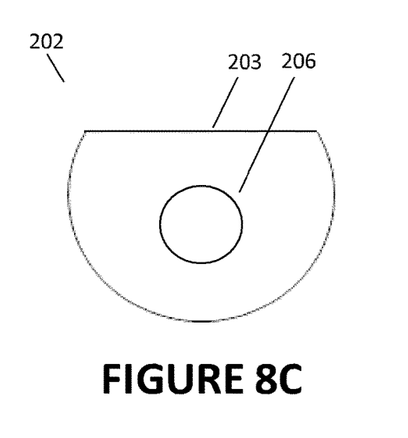
Figure 8D:
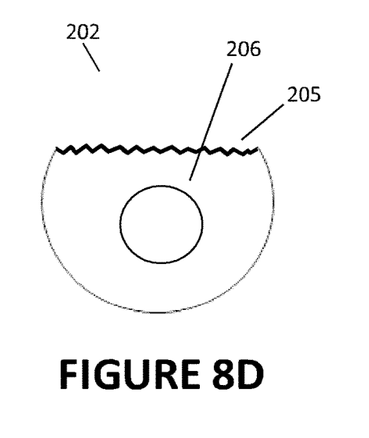

FIG. 8A shows a bottom plan view of a housing 202 for the flow generator 200. As shown, the housing 202 can have a substantially cylindrical shape. The cylindrical housing 202 may be aesthetically appealing, but the housing 202 may have a tendency to roll along the support 500 or along a surface to which the support is proximal (see FIGS. 7A-7C) when the support fixation arrangement 400 is employed, which can encourage displacement of the flow generator 200 and/or conduit extending from the gases outlet 206 of the flow generator 200. In some configurations, as seen in FIG. 8B, the housing 202 may have a substantially elliptically cylindrical shape. The elliptical shape of the housing 202 may discourage full rotation of the flow generator 200 along the support 500 or proximal surface. In some configurations, and as seen in FIG. 8C, the housing 202 may have a flat portion 203 adapted to rest against the support 500 or a proximal surface in use. The flat portion 203 of the housing 202 may additionally inhibit rotation of the flow generator 200. In some configurations, and as seen in FIG. 8D, the housing 202 may have a relatively rough portion 205 adapted to rest against the support 500 or a proximal surface in use. The relatively rough portion 205 may have a relatively high static and/or dynamic coefficient of friction to discourage rotation of the flow generator 200. In some configurations, a side of the housing 202 adapted to rest against the support 500 or a proximal surface may be padded to prevent rolling or other movements of the housing 202 along the support 500 or proximal surface from generating excess perceptible noise. Other cross-sectional shapes for housings 202 for the flow generator 200, including but not limited to square, triangular or trapezoidal shapes are contemplated.

Although the exemplary configurations are directed towards a flow generator housing or lid comprising a support fixation arrangement, it should be understood that in other configurations the support fixation arrangement may be utilized with other components of a respiratory therapy system. For example, in some configurations the same or similar support fixation arrangements may be fixed to portions of housings for respiratory therapy apparatus. The respiratory therapy apparatus housings may comprise a breathing assistance component. The breathing assistance component may comprise one or more of a blower unit, a gases humidifier, a sensor, a conduit, a filter, a muffler, a fluid reservoir, and a connector (e.g. a pneumatic, electrical, or electropneumatic connector). There may be similar advantages to housing breathing assistance components other than blower units, for example gases humidifiers, in housings with a support fixation arrangement according to any one of the described embodiments (e.g. promoting effective management of tubing, etc).

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to."

Where, in the foregoing description reference has been made to integers or components having known equivalents thereof, those integers or components are herein incorporated as if individually set forth.

The disclosed methods, apparatus and systems may also be said broadly to comprise the parts, elements and features referred to or indicated in the disclosure, individually or collectively, in any or all combinations of two or more of said parts, elements or features.

Reference to any prior art in this specification is not, and should not be taken as, an acknowledgement or any form of suggestion that that prior art forms part of the common general knowledge in the field of endeavour in any country in the world.

Although the present disclosure has been described in terms of certain embodiments, other embodiments apparent to those of ordinary skill in the art also are within the scope of this disclosure. Thus, various changes and modifications may be made without departing from the spirit and scope of the disclosure. For instance, various components may be repositioned as desired. Moreover, not all of the features, aspects and advantages are necessarily required to practice the present disclosure. Accordingly, the scope of the present disclosure is intended to be defined only by the claims that follow.

What is claimed is:

1. A respiratory therapy apparatus comprising:
a housing adapted to house breathing assistance component, comprising:
    a plurality of gases inlets configured to allow gases to enter the housing, wherein the plurality of gases inlets is distributed about a perimeter of the housing, and
    a gases outlet located on a distal end of the housing and configured to interface with a gases conduit, wherein the gases outlet is oriented such that the gases enter the plurality of gases inlets in a first direction and leave the gases outlet in a second direction,
        wherein the first direction is perpendicular to the second direction, and
        wherein the first direction is radial towards a centerline that extends through the housing;
    at least one blower configured to propel the gases from the plurality of gases inlets toward the gases outlet; and
    a support fixation arrangement adapted to attach the respiratory therapy apparatus to a support, wherein the support fixation arrangement is configured to attach the respiratory therapy apparatus such that the gases outlet is oriented downwards when in use, and wherein the support fixation arrangement is movable between a non-fixation position and a fixation position to attach the respiratory therapy apparatus to the support.

2. The respiratory therapy apparatus of claim 1, further comprising an aperture located on a proximal end of the housing, wherein the aperture is configured to provide access to the inside of the housing.

3. The respiratory therapy apparatus of claim 1, wherein at least a portion of the support fixation arrangement is fixed to or integrally formed with the housing.

4. The respiratory therapy apparatus of claim 2, wherein the respiratory therapy apparatus comprises a lid to close the aperture of the housing, and the support fixation arrangement is fixed to or integrally formed with the lid.

5. The respiratory therapy apparatus of claim 1, wherein the support fixation arrangement is located at the proximal end of the respiratory therapy apparatus.

6. The respiratory therapy apparatus of claim 1, wherein the support fixation arrangement comprises a movable tab.

7. The respiratory therapy apparatus of claim 6, wherein the tab rests in a recess.

8. The respiratory therapy apparatus of claim 1, wherein the housing is substantially cylindrical or elliptically cylindrical.

9. A respiratory therapy apparatus comprising:
a housing comprising:
    at least one gases inlet configured to allow gases to enter the housing,
    a gases outlet located on a distal end of the housing, the gases outlet configured to interface with a gases conduit,
    an aperture located on a proximal end of the housing opposite the gases outlet, wherein the aperture is configured to provide access to the inside of the housing;
a lid configured to be removably attached to the aperture of the housing, wherein the lid is proximal to the at least one gases inlet;
at least one blower configured to propel the gases from the at least one inlet toward the gases outlet; and
a support fixation arrangement adapted to attach the respiratory therapy apparatus to a support, wherein the support fixation arrangement is configured to attach the respiratory therapy apparatus such that the gases outlet is oriented downwards when in use, and wherein the support fixation arrangement is movable between a non-fixation position and a fixation position to attach the respiratory therapy apparatus to the support.

10. The respiratory therapy apparatus of claim 9, wherein the support fixation arrangement is located at a first end of the respiratory therapy apparatus and the gases outlet is located at a second end of the respiratory therapy apparatus opposite the first end.

11. The respiratory therapy apparatus of claim 9, wherein the at least one gases inlet comprises a plurality of gases inlets distributed about a perimeter of the housing.

12. The respiratory therapy apparatus of claim 9, wherein the support fixation arrangement comprises a tab secured at a first end to the housing or the lid.

13. The respiratory therapy apparatus of claim 12, wherein the tab rests in a recess on the housing or the lid when in the non-fixation position.

14. The respiratory therapy apparatus of claim 12, wherein the tab comprises a first retention element that interfaces with a second retention element on the housing or the lid to secure the tab to the housing or the lid.

15. The respiratory therapy apparatus of claim 12, wherein the tab comprises an opening configured to accept a portion of the support.

16. The respiratory therapy apparatus of claim 12, wherein the housing or lid comprises a recessed portion below the aperture such that the tab is movable through the aperture to move the tab from the non-fixation position to the fixation position.

17. The respiratory therapy apparatus of claim 9, wherein the housing is substantially cylindrical or elliptically cylindrical.

18. A respiratory therapy apparatus comprising:
a housing comprising:
at least one gases inlet configured to allow gases to enter the housing, wherein the gases inlet comprises a plurality of gases inlets distributed about a perimeter of the housing,
a gases outlet located on a distal end of the housing and is configured to interface with a gases conduit, wherein the gases outlet is oriented such that a portion of the gases entering the at least one gases inlet in a first direction and leave the gases outlet in a second direction, wherein the first direction is perpendicular to the second direction,
an aperture located on a proximal end of the housing, wherein the aperture is configured to provide access to the inside of the housing;
a lid configured to be removably attached to the aperture, wherein the lid is proximal to the at least one gases inlet;
a support fixation arrangement that is fixed to or integrally formed with the lid and is configured to attach the respiratory therapy apparatus to an external support, wherein the support fixation arrangement is configured to attach the respiratory therapy apparatus such that the gases outlet is oriented downwards when in use; and
at least one blower configured to propel the gases from the at least one inlet toward the gases outlet.

* * * * *